(12) United States Patent
Valenti

(10) Patent No.: US 11,903,776 B2
(45) Date of Patent: Feb. 20, 2024

(54) UTILITY RINGS FOR DENTAL HYGIENE

(71) Applicant: Kimberly Valenti, Brooklyn, NY (US)

(72) Inventor: Kimberly Valenti, Brooklyn, NY (US)

(*) Notice: Subject to any disclaimer, the term of this patent is extended or adjusted under 35 U.S.C. 154(b) by 0 days.

(21) Appl. No.: 17/871,052

(22) Filed: Jul. 22, 2022

(65) Prior Publication Data

US 2022/0409329 A1 Dec. 29, 2022

Related U.S. Application Data

(63) Continuation-in-part of application No. 16/865,341, filed on May 2, 2020, now Pat. No. 11,432,623.

(51) Int. Cl.
| A61B 90/53 | (2016.01) |
| A61G 15/16 | (2006.01) |
| A61C 19/00 | (2006.01) |

(52) U.S. Cl.
CPC ............ *A61B 90/53* (2016.02); *A61C 19/002* (2013.01); *A61G 15/16* (2013.01)

(58) Field of Classification Search
CPC ....... A44C 5/0007; A61C 1/145; A61C 17/08; A61C 19/001; A61C 17/06; A61C 19/00; A61C 2201/00; A61C 19/002; A61C 19/006; A44D 2203/00; A61B 90/53; A61G 15/16
See application file for complete search history.

(56) References Cited

U.S. PATENT DOCUMENTS

| 1,325,607 | A | * | 12/1919 | Barber | 206/811 |
| 4,905,335 | A | * | 3/1990 | Tervola | B25F 1/00 30/298 |
| 6,569,039 | B1 | * | 5/2003 | Cope | A63B 57/207 473/406 |
| 8,985,410 | B2 | * | 3/2015 | Wishart | A44C 5/0007 224/183 |
| 9,135,897 | B2 | * | 9/2015 | McDonald | G10D 3/173 |
| 10,172,426 | B2 | * | 1/2019 | Hsu | A44C 5/2071 |
| 2008/0311543 | A1 | * | 12/2008 | Viscomi | A61C 19/002 433/163 |
| 2011/0191945 | A1 | * | 8/2011 | Rodriguez | A41F 19/005 2/338 |
| 2011/0290833 | A1 | * | 12/2011 | Koerner | A45F 5/02 224/222 |
| 2013/0020367 | A1 | * | 1/2013 | Buckley | A63B 57/207 224/183 |
| 2013/0240694 | A1 | * | 9/2013 | Voves | B25H 3/00 248/206.5 |
| 2013/0333418 | A1 | * | 12/2013 | Anger | A44C 5/0069 63/4 |
| 2014/0110445 | A1 | * | 4/2014 | Eisner | A45F 5/00 224/222 |

(Continued)

*Primary Examiner* — David M Upchurch
(74) *Attorney, Agent, or Firm* — Steven R. Fairchild

(57) ABSTRACT

The invention is an assortment of apparatuses to magnetically tether a dental hygienist's hand to the utility tubes and hoses commonly found in a dental office. In a preferred embodiment, this is a ring containing a magnet which is worn by the hygienist. This tethers him or her finger to a utility hose or tube, which has a clasp that contains a reciprocal magnet. In another embodiment, the invention is a finger hold which contains a magnet that tether to the utility hose or tube via the magnetized clasp.

1 Claim, 15 Drawing Sheets

(56) References Cited

U.S. PATENT DOCUMENTS

| | | | |
|---|---|---|---|
| 2015/0075352 A1* | 3/2015 | McDonald | G10D 3/173 84/322 |
| 2015/0250555 A1* | 9/2015 | Haverich | A61B 90/30 600/245 |
| 2016/0003269 A1* | 1/2016 | Russell-Clarke | A44B 11/00 24/303 |
| 2016/0299526 A1* | 10/2016 | Inagaki | G06F 3/04883 |
| 2020/0328017 A1* | 10/2020 | Isenberg | B60R 11/0241 |

* cited by examiner

UTILITY RINGS FOR DENTAL HYGIENE

CROSS REFERENCE TO RELATED APPLICATION

This application claims benefit to U.S. Provisional Patent Application No. 62/536,355, filed on Jul. 24, 2017, now expired, and also claims benefit to U.S. patent application Ser. No. 16/041,751, filed on Jul. 21, 2018, now abandoned, and also claims benefit to U.S. patent application Ser. No. 16/865,341, filed on May 2, 2020, with all the foregoing incorporated herein by reference.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present invention generally relates to rings used for health and hygiene professionals to affix utility cords to the practitioner's fingers. These utility cords include cables, hoses, tubing, and the like which are commonly attached to equipment utilized by health professionals, such as dentists, hygienists, and assistants. Although the present invention comprises an entire new category of rings, in a preferred embodiment, the invention incorporates interchangeable clasps.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

Many health professionals regularly practice their art despite heavy and cumbersome cords and cables around them. For years, these health professionals had no choice but to hold these cords and cables in place while simultaneously treating patients.

For instance, dental health hygienists would wrap the cavitron tubes around their neck and secure it with their working hands. This caused great stress which made it difficult to focus one's attention on the person being treated. Further, it fatigued the finger, hands, and the arms with which the practitioner needed to treat the patient.

One product on the market, the CordEze (R) management tool, attempts to alleviate these concerns and is described in US Design Patent D818,350 to Dencek.

However, this design has many drawbacks. In particular, it has only one clip present on the wristband. It is not adjustable and allows for only one position and angle of the cord. It does not allow for any movement or rotation of the cord clip.

Further, it is difficult to put on with one hand and takes a great amount of time. The clip is too big and not adjustable for all size cords. It cannot be turned on the wrist to adjust for the angle of securement. The CordEze (R) is stiff, uncomfortable and one cannot use it for either dental hoses or tubes, such as dental unit high speed or low speed handpieces.

Further, it is difficult to place the utility cord inside the CordEze (R) wrist band. It is also painful when pressed down when the cord is pushed. Further, the CordEze (R) wrist band is not a hands-free bracelet and can get contaminated due to the constantly adjusting cord and also when removing the cord from the wrist band.

Further, due to the CordEze (R)'s elongated clip, it holds a large portion of the utility cord down to the wrist forcing the cord slack inward, which both inconveniences and distracts the health professional. Further, due to the lack of adjustability in the clip size, cords frequently slide through the clip, which shortens the cord and causes more pull. Taken together, these drawbacks require the practitioner to readjust the cord every few minutes.

Further, CordEze (R) cannot function under a lab coat, warm up jacket, or any other long sleeve garment used to protect the arms and body from harmful microorganisms.

Further, CordEze (R) can only be worn above or over the protective garments where the band is exposed to the microorganisms. Attempting to wear cordeze under a medical glove is more difficult. It needs considerate manipulation and pressure to maneuver the cord in the clip due to the glove blocking the clips entryway of the wrist band.

Further, CordEze (R) clips are large, bulky and have to be forced into the wrist band clip opening. This causes it to become contaminated. These clips can not be placed under any glove, lab coat or garment.

Further, CordEze (R) has a separate wrist band to accommodate the larger diameter hoses. There is not an all in one wrist band for both cords, hoses and tubes.

Further, the CordEze (R) wristband does not allow pivoting. The clips are locked in place and can not move. An entire separate CordEze (R) wrist band is needed to achieve pivoting. The pivoting wristband is only used for hoses and does not include any small cords.

Finally, cleaning the CordEze (R) is difficult as one cannot reach inside the clip and it is painful to the fingers while trying to clean.

A microorganism filled aerosol can constantly be dispersed in the air by dental cleanings or any work being performed in the oral cavity. Being close to the oral cavity while working contaminates any object or body next to it and exposed to it.

Dental hygienists' gloved hands are in a patients mouth, finishing a cleaning. Next the hygienist has to grab the clip placed on the tube of the handpiece, to perform a polishing. It now has to be physically pushed by hand into the wristbands clip opening to use. Even if the gloves are changed the splatter and aerosol of the polishing would contaminate it. Due to the contamination of the clips and wristbands, multiple wrist bands have to be bought so proper sterilization or disinfection requirements can be completed. The clips are big, exaggerating the wrist band and making the wrist band bulky and heavy.

The current invention alleviates many of these concerns over the prior art.

SUMMARY OF THE INVENTION

A means for magnetically tethering a hand to a dental utility device, comprising
(a) a plastic ring with a cap portion which contains a magnet;

(b) a clasp containing a magnet base and a grooved prong; and (c) the grooved prong is secured to a dental utility device. A finger grip, comprising (a) a finger grip with a magnet embedded in a top portion; and (b) a side opening that contains a series of grooved teeth.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION OF THE PREFERRED EMBODIMENTS

For a more complete understanding of the present invention, the objects and advantages thereof, reference is now made to the ensuing descriptions taken in connection with the accompanying drawings briefly described as follows.

With reference to the figures where like elements have been given like numerical designations to facilitate the reader's understanding, embodiments of the present invention are set forth below. The enclosed text and drawings are merely illustrative of one the embodiments and, as such, disclose one or more different ways of configuring the present invention. Although specific components, materials, configurations and uses are illustrated, it should be understood that a number of variations to the components and to the configuration of those components described herein and in the accompanying figures can be made without changing the scope and function of the invention set forth herein. For instance, although the figures and description provided herein show a certain game console and configurations for the components utilized with the game console, those skilled in the art will readily understand that this is merely for purposes of simplifying the present disclosure and that the present invention is not so limited.

The present invention is a class of securements for health and hygiene professionals to affix utility cords to the practitioner's hand, wrist, or forearm via adjustable silicone wristbands, rings, or fingerholds.

These utility cords include cables, hoses, tubing, and the like which are commonly attached to equipment utilized by health professionals, such as dentists, hygienists, and assistants.

Adjustable Silicone Wristband

In one embodiment, the invention utilizes an adjustable silicone utility wristband which magnetically tethers to the clasps described herein.

The wristband is made of silicone. The wristband is 9½ inches long and ¾ inches wide. The wristband is "one size fits all" and ranges and can accommodate wrists between 5¾ inches to 8½ inches in circumference.

In one embodiment, the utility band encases 2 cylinder shaped magnets that are half inch by 3/16 inches in size. In a preferred embodiment, the magnets have a pull force of approximately 11.4 pounds.

Figure 1A:
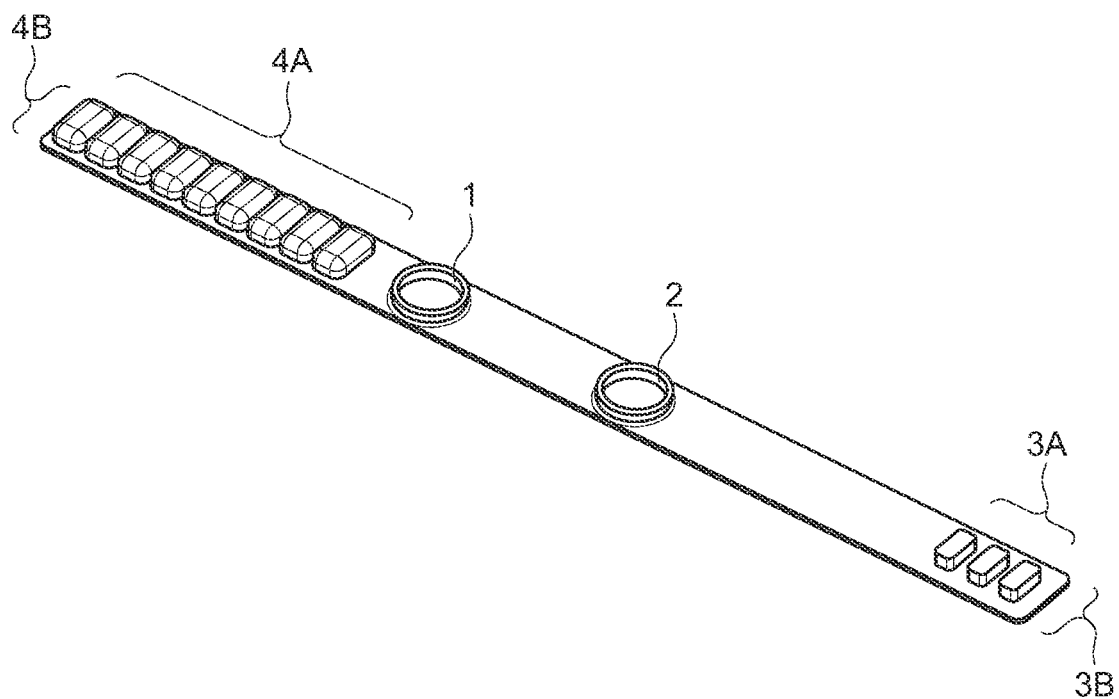
FIG. 1A and FIG. 1B depict two perspectives of the adjustable silicone utility band. These include the dorsal perspective and ventral perspective, respectively.
Figure 1B:

Reference is made to FIG. 1, which depicts two perspectives of the adjustable silicone utility band. These include the dorsal perspective (FIG. 1A) and ventral perspective (FIG. 1B).

Figure 2A:
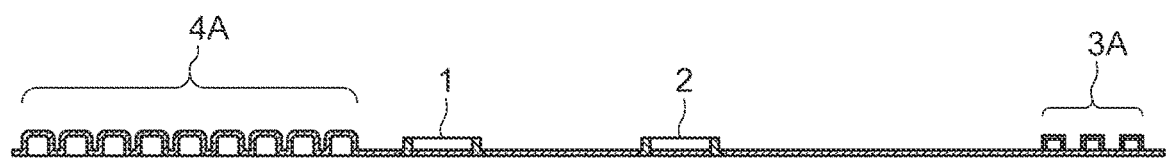
FIG. 2A and FIG. 2B depict lateral perspectives of the adjustable silicone utility band. These include a cross-sectional lateral perspective and an external lateral perspective, respectively.
Figure 2B:

Reference is made to FIG. 2, which depicts lateral perspectives of the adjustable silicone utility band. These include a cross-sectional lateral perspective (FIG. 2A) and an external lateral perspective (FIG. 2B).

As indicated in these figures, (1) is the first magnetic position on the adjustable silicone utility wristband, (2) is the second magnetic position on the adjustable silicone utility wristband, (3A) are a series of small rectangular boxes (i.e., buttons) raised on the adjustable silicone utility wristband, while (3B) is the button end of the adjustable silicone utility wristband, and (4A) are small rectangular box receptors (i.e., pockets) on the adjustable silicone utility wristband, while (4B) is the pocket end of the adjustable silicone utility wristband.

In one embodiment, there is a distance of 3¾ inches from (2) the second magnetic position to (3B) the button end of the wristband and a distance of 3¼ inches from (1) the first magnetic position magnet to (4B) the pocket end of the wristband. In a preferred embodiment, the distance between (1) the first magnetic position and (2) the second magnetic position is 1.339 inches.

On the ventral surface of the wristband there are nine pocket openings (4A), rectangular in shape. These pockets are 4 mm deep with a separation of 3.5 mm between each pocket. This is a part of the closure of the wristband.

At the dorsal surface of the wristband there are three raised rectangular buttons (3A). They are raised 4 mm high to fit tightly into the pockets (4A) present on the ventral surface. These two ends will come together and form the closure of the wristband.

In one embodiment, the pockets (4A) and buttons (3A) have a unique shape to keep it tightly closed. In a preferred embodiment, the base of the buttons (3A) are thinner and the top of the buttons (3A) are wider. The pockets (4A) are wider at the bottom of the pocket and thinner at the top of the pockets (4A). This will fit like a mold and hold the wristband securely together.

The wristband can be worn and used in multiple ways to accommodate different weights of cords and hoses and tubes. The wristband can be worn in multiple ways to accommodate all cords, hoses and tubes with different sizes and different weights.

In a preferred embodiment, the wristband is worn so that one of the two magnetic positions (1) and (2) is on top to the wrist and while the other embedded magnet is on the outer most lateral side of the wrist. The wristband can be worn in such a manner for either the right or left wrist, and for either right or left handed people.

In another embodiment, it can be worn in reverse. This will put one of the two magnetic positions (1) and (2) bottom of the wrist and the other magnet on the outer most lateral of the wrist. Basically the lateral magnet stays lateral and the wristband pivots on this point. By pivoting the wristband around at the lateral magnet, it turns and the top magnet gets switched to be the bottom magnet. The closure also gets switched from being on the bottom of the wrist to being at the top of the wrist.

The wristbands two magnetic positions (1) and (2) are located in specific sites on the wristband. Therefore each individual magnetic position will hold its proper cord, hose or tube to alleviate the maximum stress, pull and weight of all cords, hoses and tubes by using them accordingly.

The wristband has a great benefit of being worn under lab coats, jackets and gloves and still have full function and strong magnetic connection to all the clasps.

The wristband is also protected and free from contamination worn under lab coats and jacket or gloves.

Figure 4:
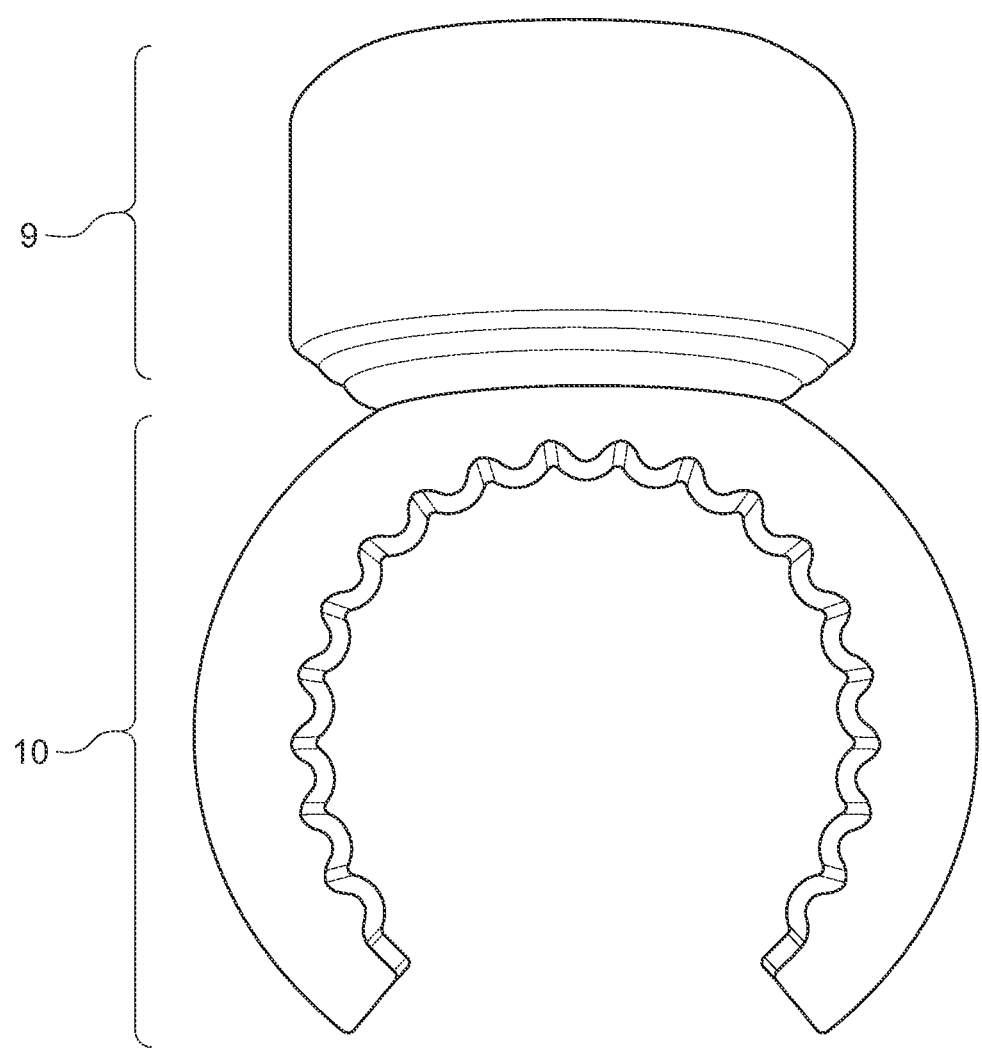
FIG. 4 depicts a lateral perspective of an assembled magnetic clasp encompassing both the magnetic rounded base and the utility cord clasp with a rounded prong.
Figure 5:
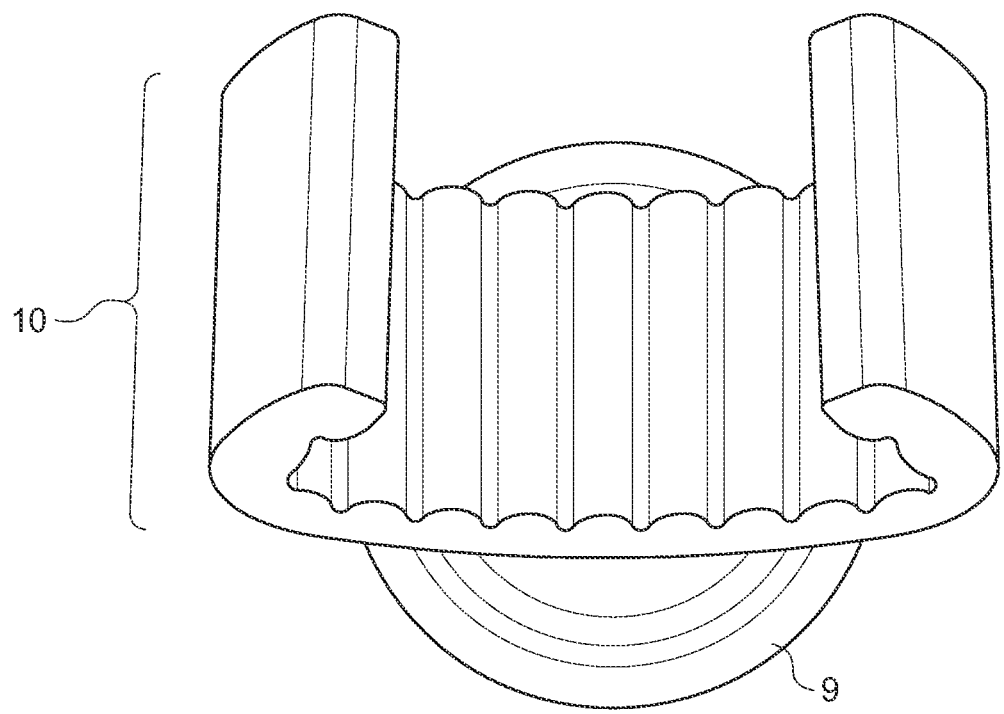
FIG. 5 depicts a top perspective of an assembled magnetic clasp encompassing both the magnetic rounded base and the utility cord clasp with a rounded prong.

In a preferred embodiment, there are four magnetic clasps for the dental hygienic cords. These have round-shaped prongs as indicated in FIG. 8. These clasps have a lumen diameter of approximately 5 mm, 6 mm, 7 mm and 8 mm. In addition there is one magnetic clasp for the dental hygienic and dental assistant largest hose. This has a round-shaped prong as indicated in FIGS. 4 and 5. This clasp has a lumen diameter of 15 mm.

Figure 6:
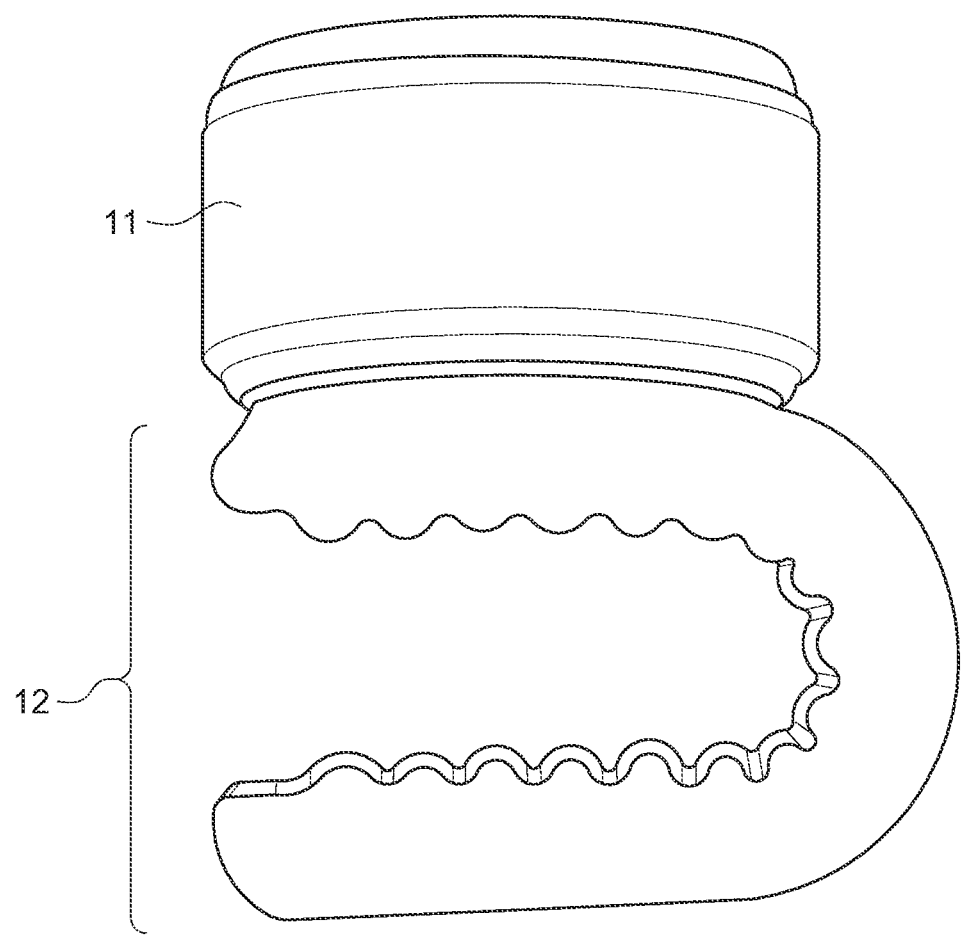
FIG. 6 depicts a lateral perspective of an assembled magnetic clasp encompassing both the magnetic rounded base and the utility cord clasp with a U-shaped prong.
Figure 7:
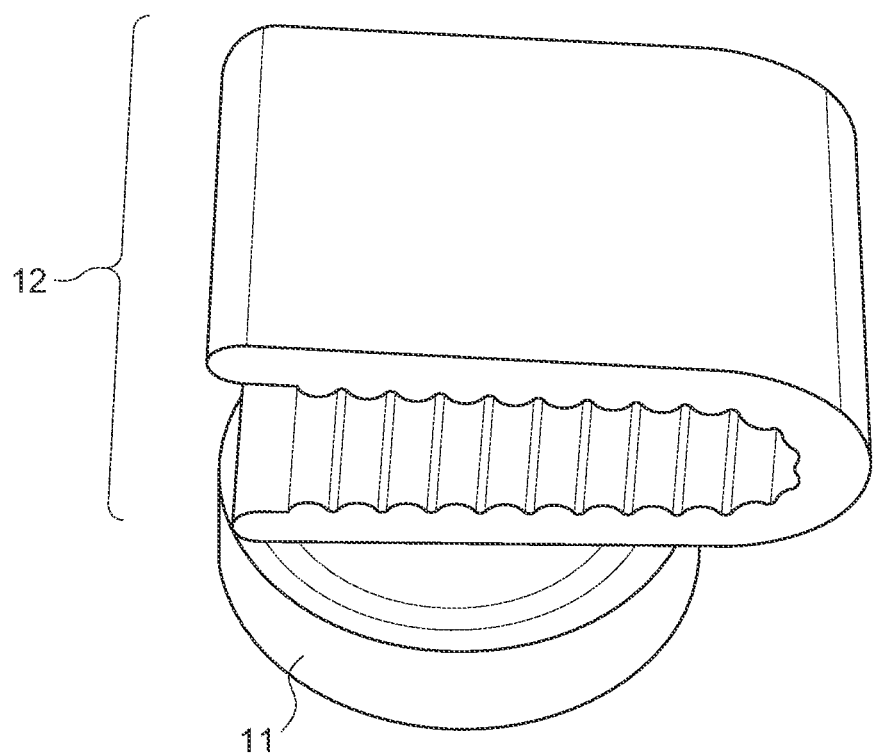
FIG. 7 depicts a top perspective of an assembled magnetic clasp encompassing both the magnetic rounded base and the utility cord clasp with a U-shaped prong.
Figure 8A:
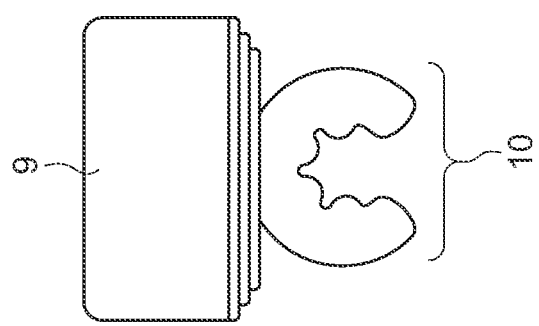
FIGS. 8A, 8B, 8C, and 8D depict a lateral perspective of four assembled magnetic clasp encompassing both the magnetic rounded base and the utility cord clasp with rounded prongs of various sizes.
Figure 8B:
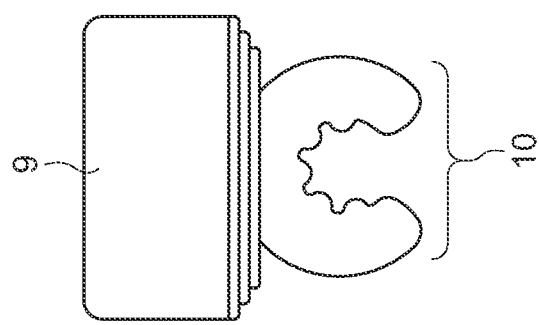
Figure 8C:
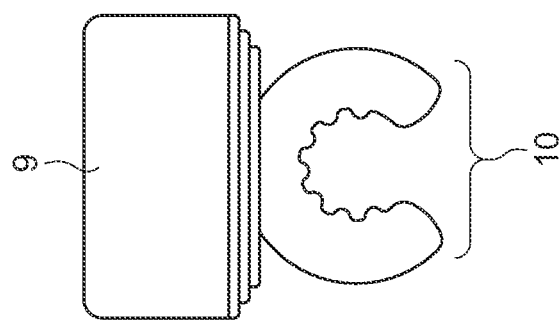
Figure 8D:
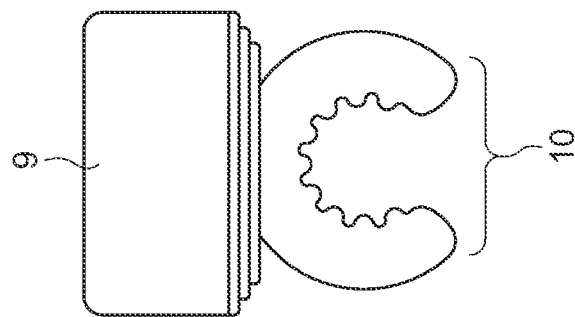

In a preferred embodiment, there are two magnetic clasps used for the dental hygienic hoses. These have U-shaped prongs as indicated in FIGS. 6 and 7. In one embodiment, the lumen diameter of the prong is approximately 7 mm wide while the total width of the same prong is approximately 13 mm. In another embodiment, the lumen of the prong is 8 mm while the total width of the prong is 13 mm.

One of the main machines with a cord used by a hygienist is the ultrasonic scaler. These machines mostly have long and very heavy cords. This cord has to be worn at the top magnet for best results. It relieves the pull and weight of the cord dramatically if not completely.

The low speed handpiece is another tool mainly used by a hygienist. The low speed handpiece is attached to the dental tray. These low speed handpiece hoses are to be worn at the outermost lateral magnet on the wristband. It naturally falls better in this position and the hose tends to be more rigid or heavier than the ultrasonic cords. This placement will relieve the pull and weight of the cord dramatically if not completely.

Another tube or hose used by a hygienist is a piezoelectric cavitron machine which uses a cord. This will be attached at the top center magnet of the wristband to relieve the pull and weight dramatically if not completely.

Another tool used is the high speed handpiece mostly used by the dentist. This has a hose just like the low speed hand piece and will be attached to the lateral magnet. This placement will relieve the pull and weight dramatically if not completely.

The wristband worn in reverse will allow magnet to be placed at the bottom of wrist. This is to hold the high-volume evacuation hoses such as the hygienist HVE hose or high speed suction hose. These will attach to the bottom magnet on the wrist. Hygienists' simultaneously use both the HVE hose in the left hand to suction and the Ultrasonic cord in the right hand, respectively to perform a prophy (hygiene cleaning).

This wristband will also be used by dental assistants for the high speed suction in the same manner. This hose will be worn at the bottom of the wrist which relieves the pull/weight dramatically if not completely from this heavy hose.

One benefit of this magnetic wrist brand is that it is allows a "hands-free" control of the cords or hoses via the clasps described above.

As a dental hygienist would understand, the cord magnet is used for such machines as the ultrasonic machine (either magnetostrictive or piezoelectric), Air polisher's, irrigators or any other machines with cords or cables. These cords are flexible and are between 5 mm to 8 mm in diameter.

In a preferred embodiment, the cord or cable magnet is located at the top of the wrist and approximately in the center of the band. It employs an 11 to 12 pound magnet to secure the connection between wristband and interchangeable magnetic clasps already attached to the cord or cable and ready to connect to the center magnet of the wristband. This can also connect to the side magnet of the wristband depending on the dental hygienist choice.

In a preferred embodiment, the hose magnet is located at the outer side of the wristband. The hose or tubing of the dental unit handpieces are larger and approximately 13 mm in diameter with more of a U-shape. Compared to cords or cables, the hoses or tubing or less are flexible and heavier.

It is envisioned that these magnets must have a magnetic pull between 11-12 pounds to ensure they stay connected during use. They will connect together by the pull of both magnets, the wristband magnet and the clasp magnet on the hose.

Interchangeable Magnetic Clasps

The invention utilizes interchangeable magnetic clasps.

Each clasp is made of a durable plastic surrounded by silicone. Each clasp is secured to a magnet. These clasps are open on one side to place and hold hoses, tubings, cords or cables, or the like commonly found in dentist offices.

The clasps maybe either U-shaped or round-shaped.

In one embodiment, the clasp has a magnet permanently attached to its ventral side, making it one piece. In a preferred embodiment, the magnet is fully embedded under the same silicone as the clasp.

The magnet secured to the clasp is cylindrically shaped.

The clasps can vary in their size circumference to properly fit the hoses, tubing, cords, and cables.

Figure 3A:
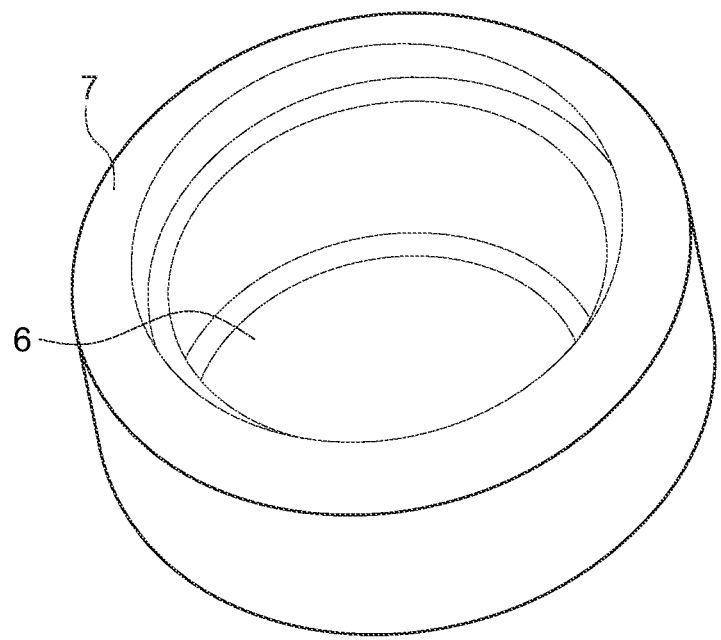
FIG. 3A and FIG. 3B depict the two portions of a magnetic clasp. These include the magnetic rounded base and the utility cord clasp, respectively.
Figure 3B:
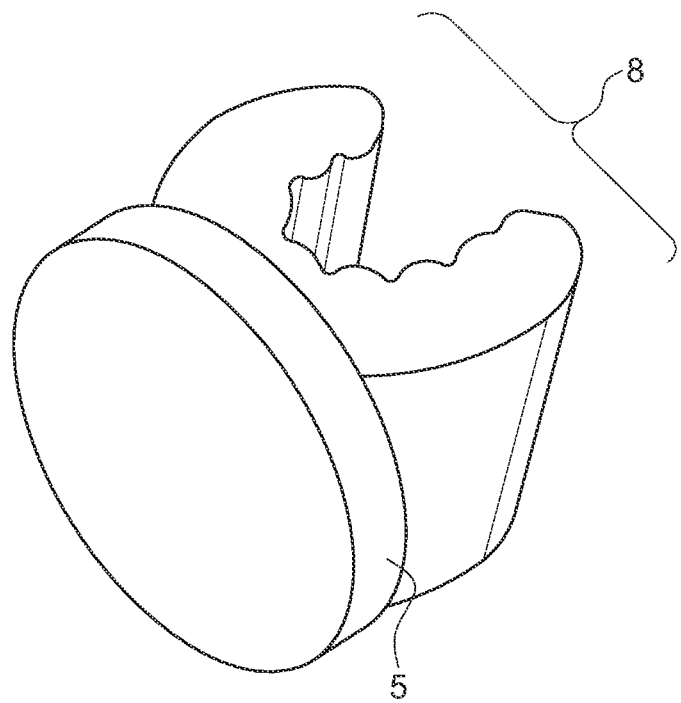

Reference is made to FIG. 3, which depicts the two portions of a magnetic clasp. These include the magnetic rounded base cap (FIG. 3A) and the utility cord clasp (FIG. 3B). The pictures depict a (5) rounded base for the utility cord clasp, a (6) pocket in the base to contain the cylindrical magnet, a (7) rounded insert for the magnetic rounded base, and a (8) portion of utility cord clasp which secures to the utility cord.

Reference is made to FIG. 4, which depicts a lateral perspective of an assembled magnetic clasp encompassing both the magnetic rounded base and the utility cord clasp with a rounded prong. Reference is also made to FIG. 5, which depicts a top perspective of an assembled magnetic clasp encompassing both the magnetic rounded base and the utility cord clasp with a rounded prong. These pictures depict a (9) magnetic base of the fully assembled magnetic clasp and a (10) utility cord clasp with a rounded prong.

Reference is made to FIG. 6, which depicts a lateral perspective of an assembled magnetic clasp encompassing both the magnetic rounded base and the utility cord clasp with a U-shaped prong. Reference is also made to FIG. 7, which depicts a top perspective of an assembled magnetic clasp encompassing both the magnetic rounded base and the utility cord clasp with a U-shaped prong. The pictures depict a (11) magnetic base of the fully assembled magnetic clasp and a (12) utility cord clasp with a U-shaped prong.

Reference is made to FIG. 8, which depicts a lateral perspective of four (FIGS. 8A, 8B, 8C, and 8D) assembled magnetic clasp encompassing both the (9) magnetic rounded base and the (10) utility cord clasp with rounded prongs of various sizes.

The hose or tubing of the dental unit handpieces are larger in size and approximately 7 mm by 13 mm and 8 mm by 13 mm in diameter and cannot be held at the top of the wrist for connection to wristband.

The high-speed suction used by the dental assistants has an even larger tube approximately 15 mm in diameter. In this instance the wristband may be moved up to the forearm due to this particular tube being less flexible.

In a preferred embodiment, the clasp size fits the precise hose, tubing, cord, or cable which the dental hygienist is employing at a particular moment.

There are four clasps for the dental hygienic cords. They are approximately 5 mm in diameter, 6 mm in diameter, 7 mm in diameter and 8 mm in diameter.

In a preferred embodiment, the clasps are tightly secured to their respective hoses, tubing, cords, or cables.

In a preferred embodiment, the clasps will be placed on the hoses, tubing, cords or cables and will stay on these items and be ready to connect. It will be pre-adjusted by the clinician for the best area on hoses or cords to clasp on for the best drag relief/weight relief They will have a clasp that will grab on the hoses or cables permanently and will then just be brought to the wrist band and snap together magnetically. The clinician can easily switch from cord to a hose or vice versa because the connectors are already in place. They can be readjusted or removed at any time. This makes it a hands-free wristband. The clinician won't have to touch the cord or hose at any time. It just has to connect by placing the wristband next to the clasp magnet.

The cap base portion of the interchangeable magnetic clasps is approximately 16 mm wide and 9 mm in height. The cap base is the same dimensions for every magnetic clasp of the invention.

The prong walls of the interchangeable magnetic clasps are approximately 3 mm thick and 10.5 mm wide. The prong diameters differ for the various sizes of this invention.

Figure 9:
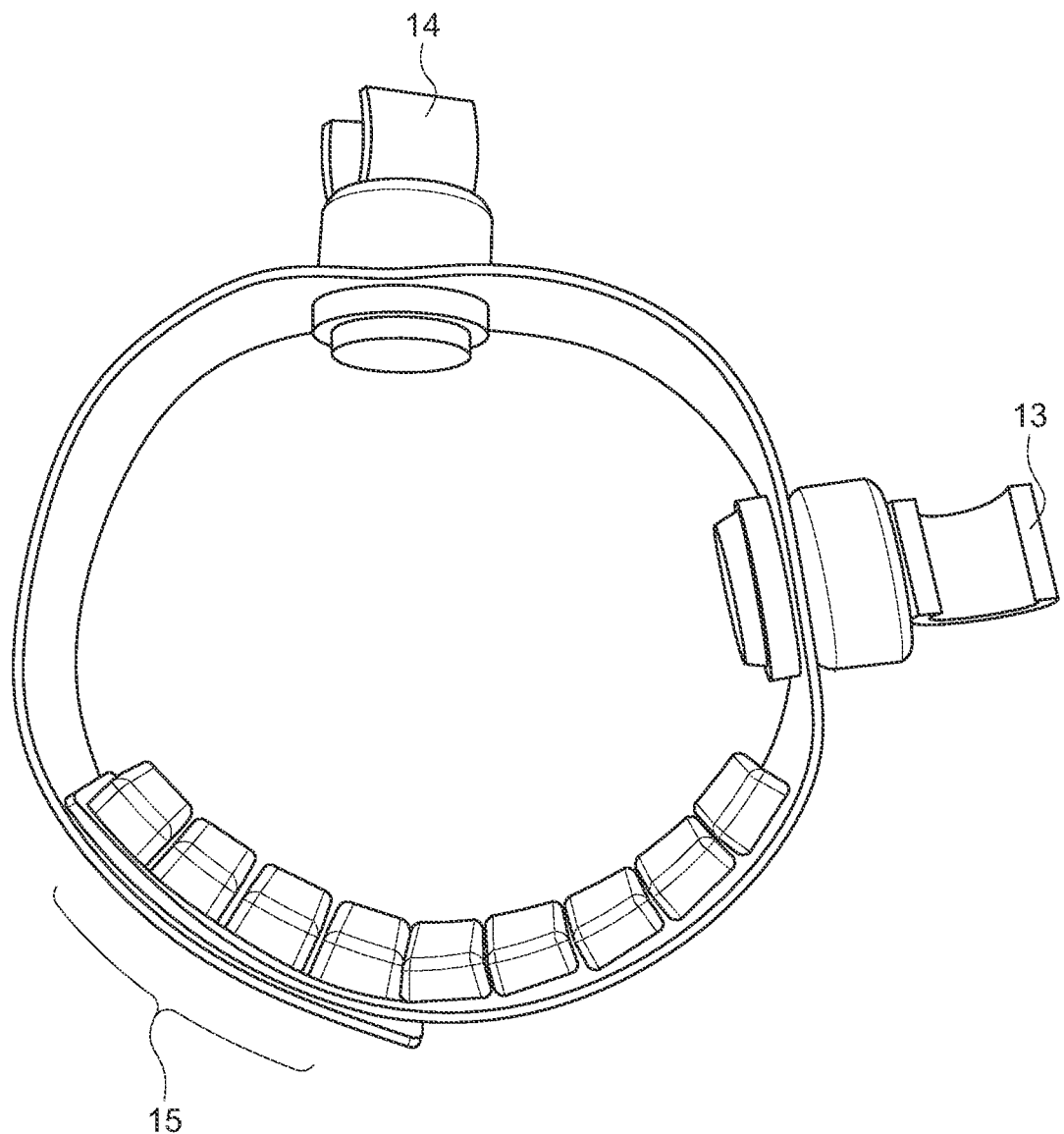
FIG. 9 depicts an adjustable silicone utility band with a fully assembled magnetic clasp and each of the two magnet positions of the utility band.
Figure 10:
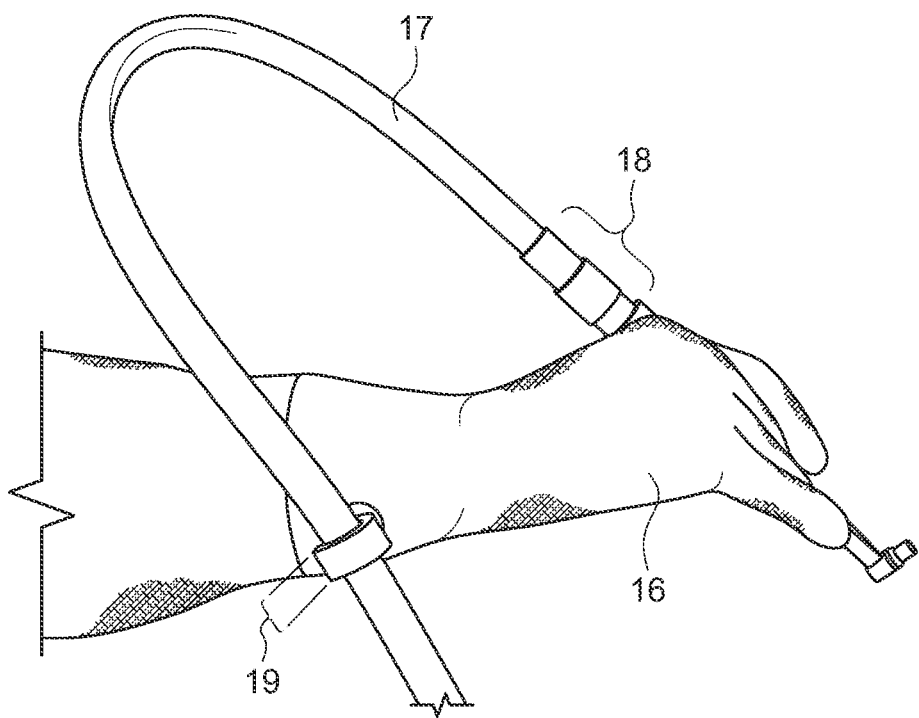
FIG. 10 depicts a dental hygienist operator using the invention with a jacket and gloved hand. The utility band is tethered to the utility "hose" through the "jacket sleeve" and glove by the magnet clasp.

Reference is made to FIG. 9, which depicts an adjustable silicone utility band with a fully assembled magnetic clasp and each of the two magnet positions of the utility band. This figure illustrates a (13) magnetic clasp secured to the first magnetic position on the utility wristband, a (14) magnetic clasp secured to the second magnetic position on the utility wristband, and (15) small rectangular boxes raised on the utility wristband secured within the small rectangular box receptors on the utility wristband Reference is made to FIG. 10, which depicts a dental hygienist operator using the invention with a gloved hand. The utility band is tethered to the utility cord through the glove by the magnetic clasp. It depicts an (16) operator's hand in a glove, a (17) utility hose, an (18) operator's tool secured to the utility hose, and a (19) utility hose secured to the operator's hand through the glove via the magnetic attachments of the invention.

Figure 11:
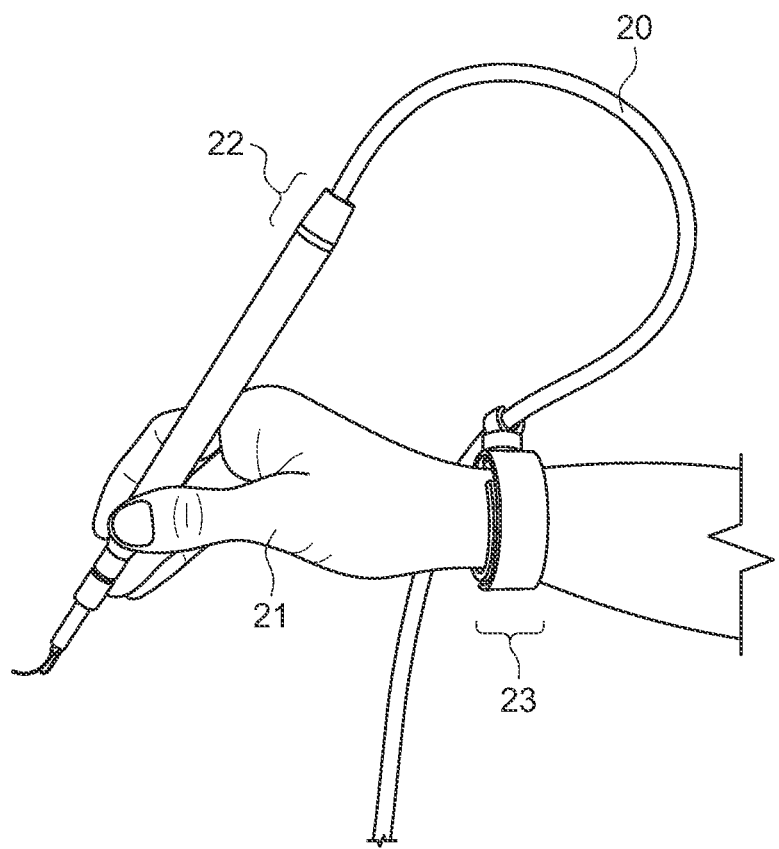
FIG. 11 depicts a dental hygienist operator using the invention with an open hand. The utility band is tethered to the utility cord by the magnetic clasp.

Reference is made to FIG. 11, which depicts a dental hygienist operator using the invention with an open hand. The utility band is tethered to the utility cord by the magnetic clasp. It depicts a (20) utility cord, an (21) operator's hand, an (22) operator's tool secured to the utility cord, and a (23) utility cord secured to the operator's hand via the magnetic attachments of the invention.

Figure 12:
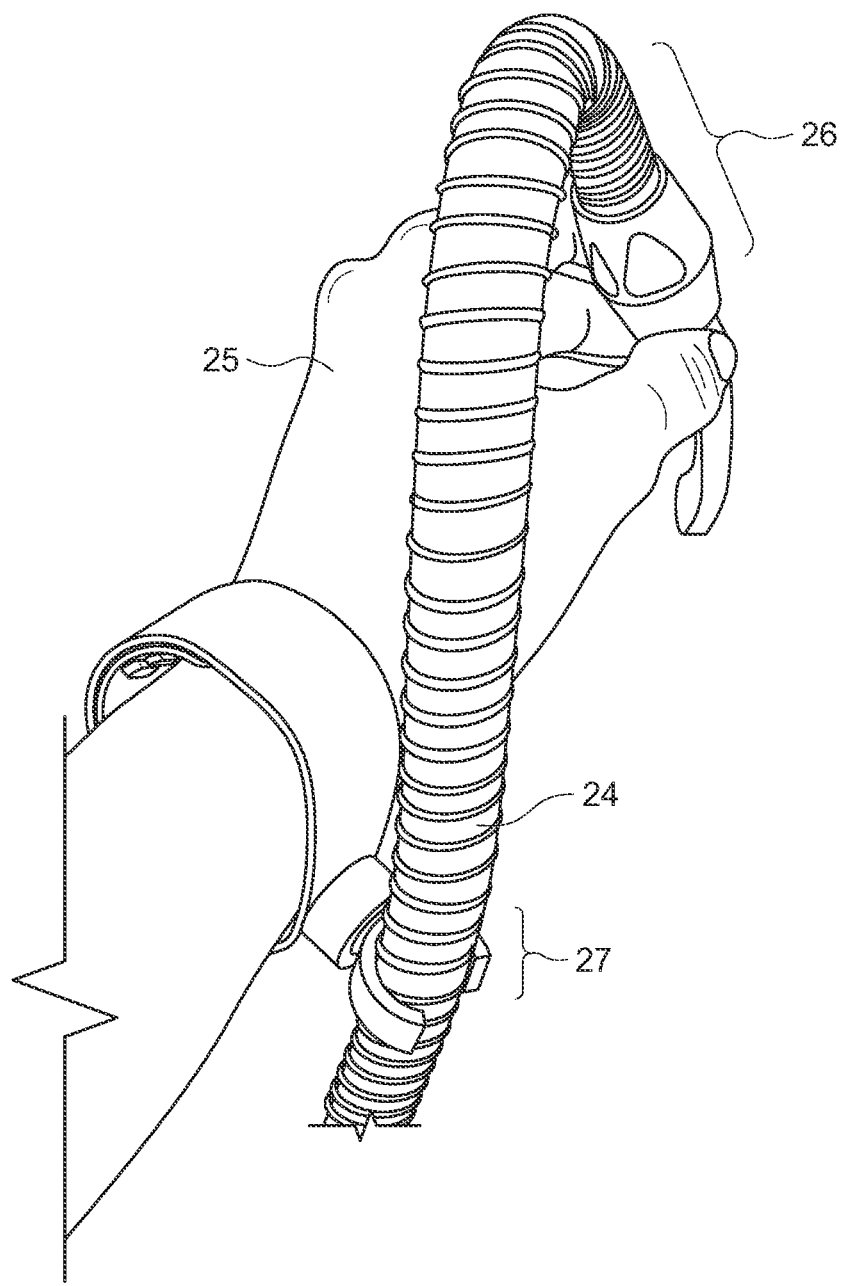
FIG. 12 depicts a dental hygienist operator using the invention with an open hand. The utility band is tethered to the utility hose by the magnetic clasp.

Reference is made to FIG. 12, which depicts a dental hygienist operator using the invention with an open hand. The utility band is tethered to the utility hose by the magnetic clasp. It depicts a (24) utility hose, an (25) operator's hand, an (26) operator's tool secured to the utility hose, and a (27) utility hose secured to the operator's hand via the magnetic attachments of the invention.

Figure 13:
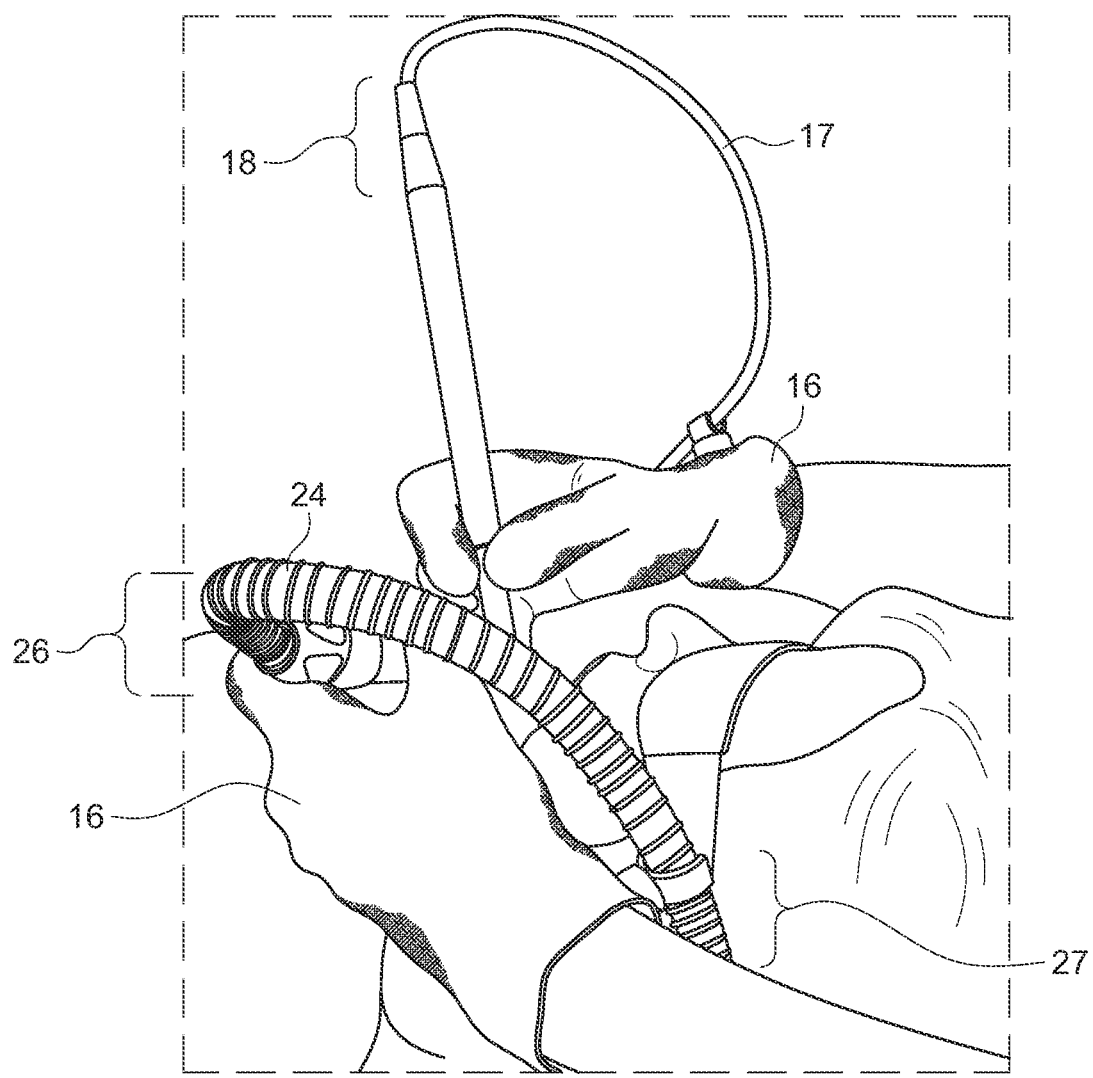
FIG. 13 depicts a dental hygienist operator using the invention in both gloved hands. As displayed with the operator's left wrist, the utility band is tethered to a utility hose through the glove by the magnetic clasp. As displayed with the operator's right wrist, the utility band is tethered to a utility cord through the glove by a magnetic clasp.

Reference is made to FIG. 13, which depicts a dental hygienist operator using the invention in both gloved hands. As displayed with the operator's left wrist, the utility band is tethered to a utility hose through the glove by the magnetic clasp. As displayed with the operator's right wrist, the utility band is tethered to a utility cord through the glove by a magnetic clasp. It depicts an (16) operator's hand in a glove, a (17) utility cord, an (18) operator's tool secured to the utility cord, and a (19) utility cord secured to the operator's hand through the glove via the magnetic attachments of the invention. It depicts a (24) utility hose, an (25) operator's hand, an (26) operator's tool secured to the utility hose, and a (27) utility hose secured to the operator's hand via the magnetic attachments of the invention.

Magnetic Silicone Rings

In one embodiment, the invention utilizes a ring with a magnet encased within. The ring is made with a durable plastic and covered in silicone.

The ring will be similarly made to the 15 mm magnetic clasp. The ring will have a cap where the magnet is placed inside and a clasp bottom that will bond together to the cap. It will be the same size cap, 9 mm×16 mm, and the same size cylindrical/discus magnet, ½ inch×³⁄₁₆ of an inch, just as all of the other magnetic clasps contain. The magnet is the same amount of pull force as well, approximately 11.4 lbs of pull force. There will be a smooth surface on all surfaces of the ring without embossments, like ripples or teeth present.

The magnetic ring comes in multiple sizes. Ring sizes can range from 5½ to 9. The ring can be worn on any of the fingers.

The magnetic ring will relieve the pull/weight of the cords, cables, hoses and tubings dramatically if not completely.

The magnetic ring will connect the cords, cables, hoses and tubings via the magnetic clasps.

The magnetic ring will connect "hands free" as well.

Figure 14A:
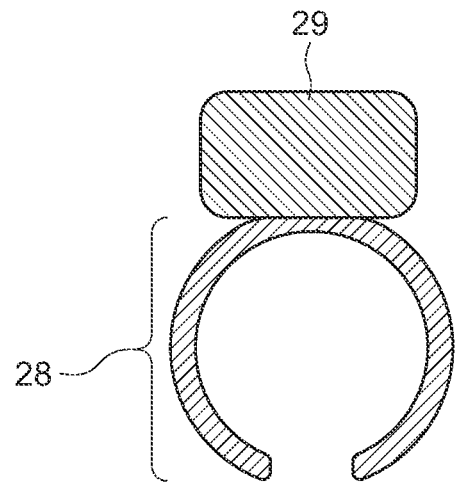
FIG. 14A and FIG. 14B depict a front view and a lateral view of a magnetic silicone ring, respectively.
Figure 14B:
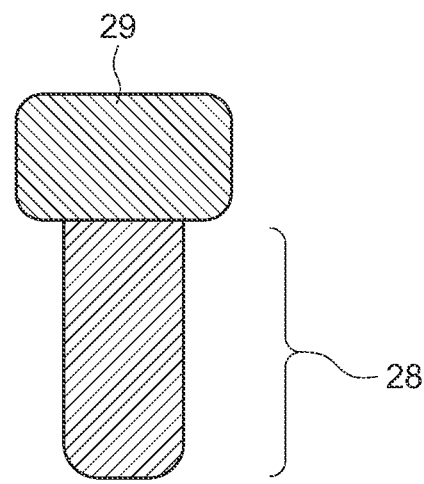

Reference is made to FIG. 14, which depicts a front view (FIG. 14A) and a lateral view (FIG. 14B) of a magnetic silicone ring. Specifically, it depicts a (28) portion of the ring that encircles the operator's finger and a (29) silicone-encased magnet.

Finger Grip

In one embodiment, the invention utilizes finger grips with magnets embedded within.

The finger grip is to be held between the fingers. It's is made of a durable plastic and surrounded by silicone. It has a ½ inch×3/16 of an inch cylindrical/discus magnet, approximately 11.4 lbs, embedded under the top portion of the finger grip.

The top portion has a magnet and also provides an opening to hold gauze. The opening has evenly raised areas of silicone teeth to hold the gauze better. The lower portion is the part to be held between the fingers. The thinner part slides between the fingers and the wider part prevents it from twisting or turning keeping it in place.

The idea is to keep it in the working hand for attaching the cords, cables, hoses or tubes to it and then switching it to the other hand to use it for the gauze hold during the hand instrumentation or scaling.

When scaling, ones put the calcareous deposits in a gauze usually held between the fingers. This could be dangerous using a sharp scaler to swipe the deposits off on the fingers. This will replace that by holding the gauze in the opening of the finger grip and swiping it there.

In another embodiment the opening is deeper and more of a pocket that is not open through to the sides.

Figure 15A:
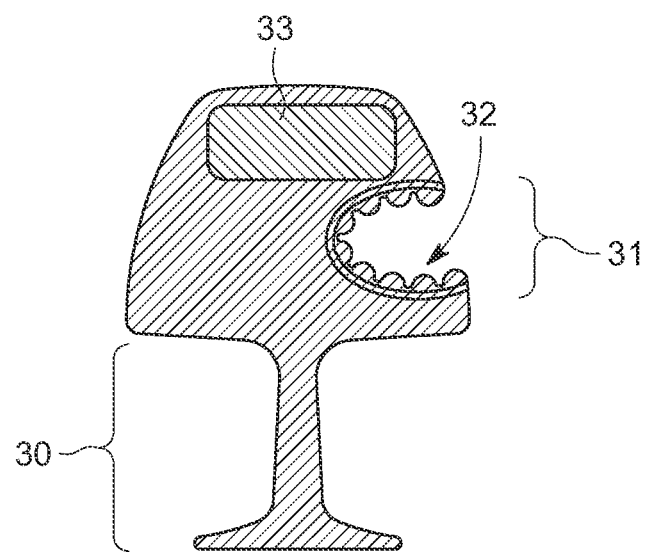
FIG. 15A and FIG. 15B depict a lateral view and a front view of a magnetic silicone finger hold, respectively.
Figure 15B:
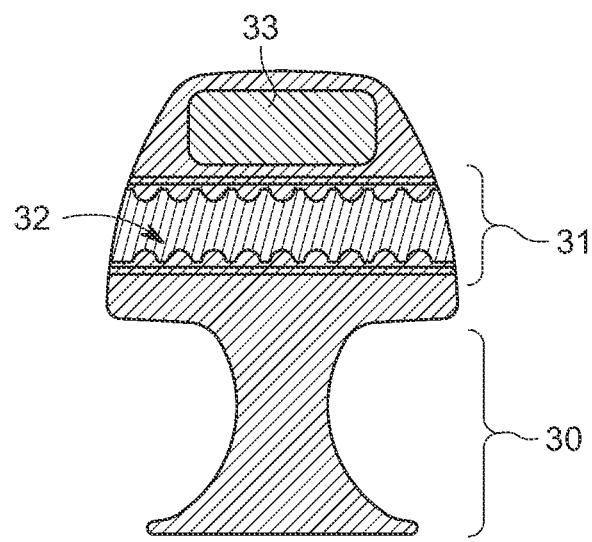

Reference is made to FIG. 15, which depicts a lateral view (FIG. 15A) and a front view (FIG. 15B) of a magnetic silicone finger hold. It depicts a (30) portion of the finger-hold which is held by the operator's finger, a (31) cavity to hold gauze, several (32) teeth within the cavity to hold gauze, and a (33) silicone enclosed magnet.

Kits

The invention also comprises a kit of the components of the adjustable silicone utility band and the clasps described above.

The kits can be selected from the group of items described above.

All components of the invention can be disinfected with OSHA compliant disinfectants which include virucidal, fungicidal, bactericidal and tuberculocidal effects for proper infection control. The sealed silicone components will allow to disinfect properly. They can be wiped down and sprayed for the recommended amount of kill time that each individual disinfectant spray has.

The foregoing description comprises illustrative embodiments of the present invention.

As will be appreciated, the foregoing objects and examples are exemplary and embodiments need not meet all or any of the foregoing objects, and need not include all or any of the exemplary features described herein. Additional aspects and embodiments within the scope of the claims will be devised by those having skill in the art based on the teachings set forth herein.

While the invention has been described in connection with what are considered to be exemplary embodiments, it is to be understood that the invention is not limited to the disclosed embodiments, but on the contrary, is intended to cover various modifications and equivalent arrangements included within the spirit and scope of the appended claims.

I claim:

1. A means for magnetically tethering a hand to a dental utility device, comprising
   (a) a plastic ring comprising a first secured magnet;
   (b) a lateral opening on a side of said plastic ring which further comprises a series of grooved teeth;
   (c) a utility hose clasp containing a second secured magnet base and a grooved prong, wherein said first secured magnet on said plastic ring magnetically tethers to said second secured magnet base on said utility hose clasp;
   (d) a dental utility device; and
   (e) a hose which is secured to said dental utility device, wherein said hose is connected to said utility hose clasp.

* * * * *